United States Patent
Shao

(10) Patent No.: US 10,960,103 B2
(45) Date of Patent: Mar. 30, 2021

(54) BONE CEMENT COMPOSITION AND KIT THEREOF

(71) Applicant: DRAGON CROWN MEDICAL CO., LTD., Shandong (CN)

(72) Inventor: Wei-Xing Shao, Shandong (CN)

(73) Assignee: DRAGON CROWN MEDICAL CO., LTD., Shandong (CN)

( * ) Notice: Subject to any disclaimer, the term of this patent is extended or adjusted under 35 U.S.C. 154(b) by 0 days.

(21) Appl. No.: 16/038,118

(22) Filed: Jul. 17, 2018

(65) Prior Publication Data
US 2019/0201575 A1 Jul. 4, 2019

(30) Foreign Application Priority Data
Jan. 4, 2018 (CN) .......................... 201810009263.7

(51) Int. Cl.
| A61L 24/06 | (2006.01) |
| A61L 24/00 | (2006.01) |
| C08K 3/30 | (2006.01) |
| C08F 299/04 | (2006.01) |

(52) U.S. Cl.
CPC .............. *A61L 24/06* (2013.01); *A61L 24/001* (2013.01); *A61L 24/0089* (2013.01); *A61L 2300/44* (2013.01); *A61L 2430/02* (2013.01); *C08F 299/04* (2013.01); *C08K 2003/3045* (2013.01); *C08K 2201/006* (2013.01)

(58) Field of Classification Search
CPC .................................................. A61L 24/0089
See application file for complete search history.

(56) References Cited

U.S. PATENT DOCUMENTS

| 5,902,839 | A | 5/1999 | Lautenschlager et al. |
| 6,800,245 | B1 | 10/2004 | Erbe et al. |
| 8,575,274 | B2 | 11/2013 | Hasenwinkel et al. |
| 9,713,654 | B2 | 7/2017 | Ueda |
| 2003/0032964 | A1* | 2/2003 | Watkins .............. A61B 17/8822 606/93 |
| 2004/0157954 | A1 | 8/2004 | Imai et al. |
| 2010/0324564 | A1* | 12/2010 | Bjursten .................. A61P 19/10 606/92 |
| 2012/0035296 | A1 | 2/2012 | Nakamura et al. |
| 2012/0046385 | A1 | 2/2012 | Nakamura et al. |
| 2013/0138114 | A1 | 5/2013 | Lin et al. |
| 2015/0056289 | A1* | 2/2015 | Ueda .................... A61L 24/0089 424/490 |
| 2015/0297467 | A1* | 10/2015 | Klee .................... C09D 133/02 523/116 |
| 2016/0106519 | A1* | 4/2016 | Hashiguchi ............. C08L 33/10 206/222 |

FOREIGN PATENT DOCUMENTS

| CN | 102333552 A | 1/2012 |
| CN | 103223188 A | 7/2013 |
| CN | 104826170 A | 8/2015 |
| CN | 106390192 A | 2/2017 |
| TW | I439298 | 6/2014 |
| TW | I444208 | 7/2014 |
| TW | I446938 | 8/2014 |
| TW | I465266 | 12/2014 |
| TW | 201544482 A | 12/2015 |
| TW | I526414 | 3/2016 |
| TW | 201742640 A | 12/2017 |
| TW | 201805028 A | 2/2018 |

OTHER PUBLICATIONS

Office Action and Search Report dated Nov. 21, 2018 issued by Taiwan Intellectual Property Office for Counterpart Application No. 107104167.
English Translation of Office Action and Search Report.
English Abstract Translation of TWI526414.
English Abstract Translation of TWI465266.
English Abstract Translation of TW201805028A.
English Abstract Translation of TW201742640A.
English Abstract Translation of TW201544482A.
English Abstract Translation of CN106390192A.
US2012046385A1 is the US counterpart to TWI446938.
US2012035296A1 is the US counterpart to TWI444208.
US2013138114A is the US counterpart to TWI439298.
Office Action from the China National Intellectual Property Administration of China patent application No. 201810009263.7, dated Jun. 1, 2020.
梁红杰等，《现代疾病临床概要与影像诊断》第1版，吉林科学技术出版社, Publication date: Apr. 30, 2014, p. 64-66.
English abstract of CN102333552A.
English abstract of CN104826170A.
English abstract of CN103223188A.

* cited by examiner

*Primary Examiner* — Michael F Pepitone
(74) *Attorney, Agent, or Firm* — WPAT, P.C., Intellectual Property Attorneys; Anthony King

(57) ABSTRACT

The present invention provides a bone cement composition. The bone cement composition includes a developing particle, an acrylic polymer, and an acrylic monomer, wherein a specific surface area of the developing particle is in a range from about 0.1 m²/g to about 5 m²/g. The present invention further provides a bone cement composition kit. The bone cement composition kit includes a power component and a liquid component, respectively stored in separate containers, wherein the power component includes a developing particle and an acrylic polymer, and the liquid component includes an acrylic monomer. A specific surface area of the developing particle is in a range from about 0.1 m²/g to about 5 m²/g.

16 Claims, No Drawings

BONE CEMENT COMPOSITION AND KIT THEREOF

BACKGROUND

The present disclosure is related to the field of orthopedics; in particular, to bone cement compositions and bone cement composition kits.

Percutaneous vertebroplasty is a minimally invasive, image-guided surgery that involves passing a bone biopsy needle from the pedicle into the vertebral body experiencing the compression fracture, followed by the injection of a bone cement, thereby preventing the continual collapse of the vertebral body. Currently, poly(methyl methacrylate) (PMMA)-based bone cement is the most common bone cement composition. Some conventional bone cement compositions may include developing particles (such as barium sulfate); however, the addition of the developing particles may reduce the moisture content of the bone cement mixture, because the conventional barium sulfate particle has a greater specific surface area and hence tends to absorb the liquid component (such as, methyl methacrylate monomers) in the bone cement mixture. The reduced moisture content of the bone cement mixture may cause the following issues: aggregation of barium sulfate particles, decreased flowability and handleability of the bone cement, and lower flexural strength.

BRIEF SUMMARY OF THE INVENTION

In view of the foregoing, the present disclosure provides a developing particle (e.g., barium sulfate) with a smaller specific surface area, thereby reducing the absorption of the liquid component in the bone cement mixture by the developing particle, and hence, increasing the handleability and flexural strength of the present bone cement.

One purpose of the present disclosure is to provide a bone cement composition that comprises a developing particle, an acrylic polymer, and an acrylic monomer, wherein the developing particle has a specific surface area in a range of about 0.1 $m^2/g$ to about 5 $m^2/g$.

Another purpose of the present disclosure is to provide a bone cement composition kit, which comprises a powder component and a liquid component, respectively stored in separate containers, wherein, the powder component comprises a developing particle and an acrylic polymer, the liquid component comprises an acrylic monomer, and the developing particle has a specific surface area in a range of about 0.1 $m^2/g$ to about 5 $m^2/g$.

A further purpose of the present disclosure is to provide a method of treating bone defect by administrating to a bone region with a defect the bone cement composition according to the present disclosure.

A further purpose of the present disclosure is to provide a method of treating bone defect by administrating to a bone region with a defect the bone cement composition kit according to the present disclosure.

Conventional developing particles, such as barium sulfate, have a greater specific surface area, and hence tends to absorb the liquid component in the bone cement mixture, thereby resulting in a decreased flowability and handleability, and lower flexural strength of the conventional bone cement. The bone cement composition and bone cement composition kit according to the present disclosure address the above-mentioned issues by reducing the specific surface area of the developing particle (e.g., barium sulfate).

DETAILED DESCRIPTION

The following disclosure provides several different embodiments, or examples, for implementing different features of the present invention. As could be appreciated, these are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

As used herein, the terms "injected," "injection," or "injectable" refer to the administration of any polymer, including injection, immersion or delivery to a subject via any delivery means.

The term "specific surface area," as used herein, refers to the sum of the area of the inner surface of the pores of the powder and the area of the outer surface of the powder per unit weight or per unit volume of the powder. The specific surface area of the powder depends on the porosity of the powder and the particle size distribution of the powder. The specific surface area of the powder is determined using the mercury intrusion porosimetry by Micromeritics Autopore.

One purpose of the present disclosure is to provide a bone cement composition that comprises a developing particle, an acrylic polymer, and an acrylic monomer, wherein the developing particle has a specific surface area in a range of about 0.1 $m^2/g$ to about 5 $m^2/g$.

Another purpose of the present disclosure is to provide a bone cement composition kit, which comprises a powder component and a liquid component, respectively stored in separate containers, wherein, the powder component comprises a developing particle and an acrylic polymer, the liquid component comprises an acrylic monomer, and the developing particle has a specific surface area in a range of about 0.1 $m^2/g$ to about 5 $m^2/g$.

According to one embodiment, in the bone cement composition of the present disclosure and the bone cement composition kit of the present disclosure, the specific surface area of the developing particle is in a range of about 0.1 m$^2$/g to about 5 m$^2$/g. Preferably, the specific surface area of the developing particle is in a range of about 0.1 m$^2$/g to about 3 m$^2$/g. More preferably, the specific surface area of the developing particle is in a range of about 0.1 m$^2$/g to about 2 m$^2$/g.

According to one embodiment, in the bone cement composition and bone cement composition kit of the present disclosure, illustrative examples of the developing particle include, but are not limited to, barium sulfate, zirconium oxide, thallium, titanium dioxide, 153Sm, triphenyl-bismuthin, iodixanol, and iohexol. According to one embodiment, the developing particle is preferably barium sulfate or zirconium oxide.

According to one embodiment, in the bone cement composition of the present disclosure and the bone cement composition kit of the present disclosure, the developing particle is provided in an amount in a range of about 5 wt % to about 45 wt %, based on the total weight of the bone cement composition or the bone cement composition kit. Preferably, the developing particle is provided in an amount in a range of about 10 wt % to about 35 wt %, based on the total weight of the bone cement composition or the bone cement composition kit. More preferably, the developing particle is provided in an amount in a range of about 20 wt % to about 30 wt %, based on the total weight of the bone cement composition or the bone cement composition kit.

According to one embodiment, in the bone cement composition and bone cement composition kit of the present disclosure, the ratio of the acrylic polymer to the acrylic monomer is in a range from about 0.5 (g/g) to about 3.5 (g/g). Preferably, the ratio of the acrylic polymer to the acrylic monomer is in a range from about 1 (g/g) to about 2.5 (g/g). More preferably, the ratio of the acrylic polymer to the acrylic monomer is in a range from about 1.5 (g/g) to about 2.0 (g/g).

According to one embodiment, in the bone cement composition kit of the present disclosure, the ratio of the powder component to the liquid component is in a range from about 1.3 (g/g) to about 3.5 (g/g). Preferably, the ratio of the powder component to the liquid component is in a range from about 1.8 (g/g) to about 3.0 (g/g). More preferably, the ratio of the powder component to the liquid component is in a range from about 2.3 (g/g) to about 2.5 (g/g).

According to one embodiment, the bone cement composition of the present disclosure comprises an acrylic polymer. According to one embodiment, in the bone cement composition kit of the present disclosure, the powder component comprises an acrylic polymer. The acrylic polymer is formed by the polymerization of acrylic monomer as the polymerizable monomer, examples of which include, but are not limited to, (A) poly(alkyl acrylates) such as such as, poly(methyl methacrylate)(PMMA), poly(ethyl methacrylate) (PEMA), poly(butyl methacrylate) (PBMA), poly(methyl acrylate) (PMA), etc.; these polymers are formed from the polymerization of alkyl acrylate-based monomer, such as, methyl acrylate (MA), methyl methacrylate (MMA), ethyl methacrylate (EMA), butyl methacrylate, etc.; (B) copolymers formed from the copolymerization of methyl acrylate (MA) or methyl methacrylate with at least one monomer selected from styrene, ethyl methacrylate, and methyl acrylate; and (C) polymers formed from the polymerization of dimethyl acrylate-based monomer, such as bisphenol A-diglycidyl dimethacrylate (Bis-GMA), 2,2-bis[4- (3-methyl propenoxy-2-hydroquinone propoxyl)phenyl] propane, 2,2-bis(4-methylpropenoxyethoxyphenyl)propane (Bis-MEPP), triethylene glycol dimethacrylate (TEGDMA), diethylene glycol dimethacrylate (DEGDMA), ethylene glycol dimethacrylate (EGDMA), etc. According to one embodiment, the bone cement composition and the bone cement composition kit of the present disclosure preferably comprises poly(methyl methacrylate) or copolymers formed using methyl methacrylate as the polymerizable monomer.

According to one embodiment, the bone cement composition of the present disclosure comprises an acrylic monomer. According to one embodiment, in the bone cement composition kit of the present disclosure, the liquid component comprises an acrylic monomer. The acrylic monomer is mixable with the above-mentioned acrylic polymer, thereby allowing the polymerization of the polymerizable monomer (such as, methyl acrylate monomer), which in turn hardens the bone cement composition. Illustrative examples of the acrylic monomer include, but are not limited to, alkyl acrylate-based monomer, dimethyl acrylate-based monomer, etc. Preferred examples of the acrylic monomer are methyl methacrylate (MMA), ethyl methacrylate (EMA), butyl methacrylate, methyl acrylate (MA), etc. Preferred examples of the dimethyl acrylate-based monomer are bisphenol A-diglycidyl dimethacrylate (Bis-GMA), 2,2-bis[4-(3-methyl propenoxy-2-hydroquinone propoxyl)phenyl]propane, 2,2-bis(4-methylpropenoxyethoxyphenyl)propane (Bis-MEPP), triethylene glycol dimethacrylate (TEGDMA), diethylene glycol dimethacrylate (DEGDMA), ethylene glycol dimethacrylate (EGDMA), etc.

According to one embodiment, the bone cement composition of the present disclosure further comprises a polymerization initiator and a polymerization promoter capable of promoting the polymerization of the acrylic polymer, or a polymerization inhibitor capable of inhibiting the polymerization of the acrylic polymer.

According to one embodiment, the bone cement composition kit of the present disclosure further comprises a polymerization initiator and a polymerization promoter capable of promoting the polymerization of the acrylic polymer with the proviso that the polymerization initiator and the polymerization promoter are not provided in the same component at the same time.

According to one embodiment, in the bone cement composition kit of the present disclosure, the polymerization initiator may be provided in the powder component comprising the developing particle and the acrylic polymer or the liquid component comprising the acrylic monomer.

According to one embodiment, in the bone cement composition kit of the present disclosure, the polymerization promoter may be provided in the powder component comprising the developing particle and the acrylic polymer or the liquid component comprising the acrylic monomer.

According to one embodiment, in the bone cement composition kit of the present disclosure, the powder component and the liquid component are respectively stored in separate containers, and the polymerization initiator and the polymerization promoter are respectively added into the powder component and the liquid component. In this way, only when a mixture comprising the powder component and the liquid component is formed, will the polymerization initiator and the polymerization promoter come into contact and trigger the polymerization, whereas the portions that are not mixed will not be polymerized.

According to one embodiment, in the bone cement composition kit of the present disclosure, the liquid component may further comprise a polymerization inhibitor.

According to one embodiment, illustrative examples of the polymerization initiator include, but are not limited to, benzoyl peroxide, tert-butyl hydroperoxide, lauroyl peroxide, azobisisobutyronitrile, and a mixture thereof. According to one embodiment, the polymerization initiator is preferably benzoyl peroxide.

According to one embodiment, illustrative examples of the polymerization promoter include, but are not limited to, N,N-dimethyl-p-toluidine (DMPT), 2,4,6-tris(dimethylaminomethyl)phenol, and a mixture thereof. According to one embodiment, the polymerization promoter is preferably N,N-dimethyl-p-toluidine.

According to one embodiment, in the bone cement composition kit of the present disclosure, the liquid component may further comprise a polymerization inhibitor. Illustrative examples of the polymerization inhibitor include, but are not limited to, hydroquinone (HQ), methyl hydroquinone (MEHQ), and ascorbic acid.

According to one embodiment, the bone cement composition of the present disclosure may further comprise a bone matrix, wherein the bone matrix can be an inorganic bone substituent that is osteogenic; for example, the bone matrix may have a main constituent that is a phosphate, sulfate, bioglass ($Na_2O$—$CaO$—$SiO_2$—$P_2O_5$) or a mixture thereof.

According to one embodiment, in the bone cement composition kit of the present disclosure, the powder component may further comprise a bone matrix, wherein the bone matrix can be an inorganic bone substituent that is osteogenic; for example, the bone matrix may have a main constituent that is a phosphate, sulfate, bioglass ($Na_2O$—$CaO$—$SiO_2$—$P_2O_5$) or a mixture thereof.

According to one embodiment, the main constituent is a phosphate selected from the group consisting of, hydroxyapatite (HA), β-tricalcium phosphate (β-TCP), tetracalcium phosphate, calcium hydrogen phosphate ($CaHPO_4$), octacalcium phosphate ($Ca_8H_2(PO_4)_6 \cdot 5H_2O$), calcium pyrophosphate ($Ca_2P_2O_7$), amorphous calcium phosphate (ACP), magnesium dihydrogen phosphate, magnesium hydrogen phosphate, magnesium phosphate, magnesium ammonium phosphate, magnesium ammonium phosphate hexahydrate, strontium phosphate, strontium hydrogen phosphate, strontium dihydrogen phosphate, and a mixture thereof.

According to one embodiment, the main constituent is a sulfate selected from the group consisting of, calcium sulfate dihydrate, calcium sulfate hemihydrate, calcium sulfate anhydrate, magnesium sulfate, magnesium sulfate monohydrate, magnesium sulfate heptahydrate, strontium sulfate, and a mixture thereof.

According to one embodiment, the bone cement composition of the present disclosure and the bone cement composition kit of the present disclosure may further comprise small-molecule osteoinductive drugs, such as corticosteroids, oxidized steroids, etc.

According to one embodiment, the bone cement composition of the present disclosure and the bone cement composition kit of the present disclosure may further comprise an osteogenic material, such as, living cell sources, e.g., stem cells, multipotent cells, pluripotent cells, osteoprogenitor cells, preosteoblasts, mature osteoblasts, and a mixture thereof, and the like.

According to one embodiment, the bone cement composition of the present disclosure and the bone cement composition kit of the present disclosure do not comprise any conventional vehicle. Said vehicle is a pharmaceutically inert substance; conventional vehicles include, cellulose, cellulose derivatives, methyl cellulose, sodium carboxymethyl cellulose, carboxymethyl cellulose (CMC), hydroxyethyl cellulose (HEC), ethyl cellulose, hydroxypropyl cellulose (HPC), hydroxypropyl methyl cellulose (HPMC), glycerol, polyethylene glycol (PEG), polyethylene glycol 600 (PEG600), polyethylene glycol 4000 (PEG4000), glycosaminoglycan, hyaluronan, chondroitin sulfate and derivatives thereof, collagen, gelatin, ethylene glycol, propylene glycol, polyhydroxyalkanoate (PHA), polylactic acid (PLA), polyglycolic acid (PGA), poly(lactic-co-glycolic acid) (PLGA), polycaprolactone (PCL), and a mixture thereof.

According to one embodiment, the bone cement composition of the present disclosure and bone cement composition kit of the present disclosure may be used to prepare a medical composition for treating bone defects. According to one embodiment, the medical composition prepared using the bone cement composition and bone cement composition kit of the present disclosure can be used to repair and fill various bone defects. According to one embodiment, the term "bone defect" refers to any bone regions with a defect, such as voids, cracks, notches, or any other discontinuity in the bone. For example, said bone defect may be caused by any of the following factors, osteoporotic vertebral compression fractures, ischemic bone necrosis, cavity within the spinal cord caused by benign or malignant osteoma, bone collapse, deformation of the bone structure, bone defects resulted from traumas, bone defects resulted from limb or craniofacial surgeries, etc.

As could be appreciated by persons having ordinary skill in the art, in addition to those described in the previous embodiments, the bone cement composition and bone cement composition kit of the present disclosure can be used in many other applications. Persons having ordinary skill in the art should also understand that these detailed descriptions and appended drawings are provided for the illustrative purpose and shall not be construed as limiting to the scope of the present invention. Those skilled in the art should also realize that they may make various changes, substitutions, and alterations herein without departing from the spirit and scope of the present disclosure. The scope of the present disclosure shall only be limited to the appended claims.

EXAMPLES

Specific examples of the present disclosure are provided below; however, the present disclosure is not limited to these specific examples.

In the following specific examples, the amount of each component is expressed as the weight percent (wt %).

Comparative Example 1

Preparation of Bone Cement Composition 1

35% barium sulfate, 0.4% benzoyl peroxide (BPO), and 64.6% poly(methyl methacrylate) were mixed to form a powder component, wherein the total weight of the powder component was 25 g. In this comparative example, the total pore area of the barium sulfate was 14.8 m²/g. Also, the viscosity of poly(methyl methacrylate) was 145 ml/g with a central particle size of 55 μm and having 0.4% BPO.

Further, 98.8% methyl methacrylate, 0.002% hydroquinone, and 1.2% N,N-dimethyl-p-toluidine (DMPT) were mixed to form a liquid component, wherein the total volume of the liquid component was 10.64 mL.

Finally, the above-mentioned powder component and liquid component were mixed under a temperature of 23° C.±1° C. to form the bone cement composition 1. Start timing upon the contact of the powder component and the liquid component, and at 2 minutes±10 seconds after the start of the mixing process, 1 mL of the bone cement composition 1 was collected and placed on a glass panel that was rested horizontally; then the glass panel was tilted by 40 degrees immediately, and the distance by which the bone cement composition 1 flowed was recorded. The remainder of the bone cement composition 1 was filled into a mold after the composition became doughy, and the flexural strength was determined in accordance with the ISO 5833 standard.

The distance by which the bone cement composition 1 flowed was less than 0.1 mm, and the bone cement composition 1 formed a dried agglomerate with poor handleability. The flexural strength of the bone cement composition 1 was 31.8±3.9 MPa.

Example I

Preparation of Bone Cement Composition 2

35% barium sulfate, 0.4% benzoyl peroxide, and 64.6% poly(methyl methacrylate) were mixed to form a powder component, wherein the total weight of the powder component was 25 g. In this example, the total pore area of the barium sulfate was 1.7 m²/g. Also, the viscosity of the poly(methyl methacrylate) was 145 ml/g with a central particle size of 55 μm and having 0.4% BPO.

Further, 98.8% methyl methacrylate, 0.002% hydroquinone, and 1.2% N,N-dimethyl-p-toluidine (DMPT) were mixed to form a liquid component, wherein the total volume of the liquid component was 10.64 mL.

Finally, the above-mentioned powder component and liquid component were mixed under a temperature of 23° C.±1° C. to form the bone cement composition 2. Start timing upon the contact of the powder component and the liquid component, and at 2 minutes±10 seconds after the start of the mixing process, 1 mL of the bone cement composition 2 was collected and placed on a glass panel that was rested horizontally; then the glass panel was tilted by 40 degrees immediately, and the distance by which the bone cement composition 2 flowed was recorded. The remainder of the bone cement composition 2 was filled into a mold after the composition became doughy, and the flexural strength was determined in accordance with the ISO 5833 standard.

The distance by which the bone cement composition 2 flowed was 1.1±0.1 mm, and the bone cement composition 2 formed a soft agglomerate. The flexural strength of the bone cement composition 2 was 46.4±0.9 MPa.

Example II

Preparation of Bone Cement Composition 3

35% barium sulfate, 0.4% benzoyl peroxide, and 64.6% poly(methyl methacrylate) were mixed to form a powder component, wherein the total weight of the powder component was 25 g. In this example, the total pore area of the barium sulfate was 0.37 m²/g. Also, the viscosity of the poly(methyl methacrylate) was 145 ml/g with a central particle size of 55 μm and having 0.4% BPO.

Further, 98.8% methyl methacrylate, 0.002% hydroquinone, and 1.2% N,N-dimethyl-p-toluidine (DMPT) were mixed to form a liquid component, wherein the total volume of the liquid component was 10.64 mL.

Finally, the above-mentioned powder component and liquid component were mixed under a temperature of 23° C.±1° C. to form the bone cement composition 3. Start timing upon the contact of the powder component and the liquid component, and at 2 minutes±10 seconds after the start of the mixing process, 1 mL of the bone cement composition 3 was collected and placed on a glass panel that was rested horizontally; then the glass panel was tilted by 40 degrees immediately, and the distance by which the bone cement composition 3 flowed was recorded. The remainder of the bone cement composition 3 was filled into a mold after the composition became doughy, and the flexural strength was determined in accordance with the ISO 5833 standard.

The distance by which the bone cement composition 3 flowed was 42±4 mm, and the bone cement composition 3 formed a sticky liquid. The flexural strength of the bone cement composition 3 was 52.7±3.5 MPa.

Example III

Preparation of Bone Cement Composition 4

35% barium sulfate, 0.4% benzoyl peroxide, and 64.6% poly(methyl methacrylate) were mixed to form a powder component, wherein the total weight of the powder component was 25 g. In this example, the total pore area of the barium sulfate was 4.79 m²/g. Also, the viscosity of the poly(methyl methacrylate) was 145 ml/g with a central particle size of 55 μm and having 0.4% BPO.

Further, 98.8% methyl methacrylate, 0.002% hydroquinone and 1.2% N,N-dimethyl-p-toluidine (DMPT) were mixed to form a liquid component, wherein the total volume of the liquid component was 10.64 mL.

Finally, the above-mentioned powder component and liquid component were mixed under a temperature of 23° C.±1° C. to form the bone cement composition 4. Start timing upon the contact of the powder component and the liquid component, and at 2 minutes±10 seconds after the start of the mixing process, 1 mL of the bone cement composition 4 was collected and placed on a glass panel that was rested horizontally; then the glass panel was tilted by 40 degrees immediately, and the distance by which the bone cement composition 4 flowed was recorded. The remainder of the bone cement composition 4 was filled into a mold after the composition became doughy, and the flexural strength was determined in accordance with the ISO 5833 standard.

The distance by which the bone cement composition 4 flowed was 0.7±0.1 mm, and the bone cement composition 4 formed a sticky liquid. The flexural strength of the bone cement composition 4 was 44.6±3.6 MPa.

What is claimed is:

1. A bone cement composition, comprising a developing particle, an acrylic polymer, and an acrylic monomer, wherein the developing particle includes barium sulfate, zirconium oxide, thallium, titanium dioxide, 153Sm, triphenyl-bismuthin, iodixanol, iohexol, or a combination thereof, and the developing particle has a specific surface area in a range of 0.1 m²/g to 0.4 m²/g.

2. The bone cement composition according to claim 1, wherein the ratio of the acrylic polymer to the acrylic monomer is in a range from about 0.5 (g/g) to about 3.5 (g/g).

3. The bone cement composition of claim 1, further comprising a polymerization initiator, wherein the polymerization initiator is selected from the group consisting of benzoyl peroxide, tert-butyl hydroperoxide, lauroyl peroxide, azobisisobutyronitrile, and a mixture thereof.

4. The bone cement composition of claim 1, further comprising a polymerization promoter, wherein the polymerization promoter is selected from the group consisting of N,N-dimethyl-p-toluidine, 2,4,6-tris(dimethylaminomethyl) phenol, and a mixture thereof.

5. The bone cement composition of claim 1, further comprising a polymerization inhibitor, wherein the polymerization inhibitor is selected from the group consisting of hydroquinone (HQ), methyl hydroquinone (MEHQ), ascorbic acid, and a mixture thereof.

6. The bone cement composition of claim 1, wherein the acrylic polymer is selected from the group consisting of (A) poly(alkyl acrylates) formed from the polymerization of alkyl acrylate-based monomers; (B) copolymers formed from the copolymerization of methyl acrylate or methyl methacrylate with at least one monomer selected from styrene, ethyl methacrylate, and methyl acrylate; and (C) polymers formed from the polymerization of dimethyl acrylate-based monomers.

7. The bone cement composition of claim 1, wherein the acrylic monomer is selected from the group consisting of methyl methacrylate (MMA), ethyl methacrylate (EMA), butyl methacrylate, methyl acrylate (MA), bisphenol A-diglycidyl dimethacrylate (Bis-GMA), 2,2-bis[4-(3-methyl propenoxy-2-hydroquinone propoxyl)phenyl]propane, 2,2-bis(4-methylpropenoxyethoxyphenyl)propane (Bis-MEPP), triethylene glycol dimethacrylate (TEGDMA), diethylene glycol dimethacrylate (DEGDMA), ethylene glycol dimethacrylate (EGDMA), and a combination thereof.

8. A bone cement composition kit, comprising a powder component and a liquid component, respectively stored in separate containers, wherein the powder component comprises a developing particle and an acrylic polymer, the liquid component comprises an acrylic monomer, the developing particle includes barium sulfate, zirconium oxide, thallium, titanium dioxide, 153Sm, triphenyl-bismuthin, iodixanol, iohexol, or a combination thereof, and the developing particle has a specific surface area in a range of 0.1 $m^2/g$ to 0.4 $m^2/g$.

9. The bone cement composition kit of claim 8, wherein the ratio of the powder component to the liquid component is in a range from about 1.3 (g/g) to about 3.5 (g/g).

10. The bone cement composition kit of claim 8, further comprising a polymerization initiator, wherein the polymerization initiator is selected from the group consisting of benzoyl peroxide, tert-butyl hydroperoxide, lauroyl peroxide, azobisisobutyronitrile, and a mixture thereof.

11. The bone cement composition kit of claim 8, further comprising a polymerization promoter, wherein the polymerization promoter is selected from the group consisting of N,N-dimethyl-p-toluidine, 2,4,6-tris(dimethylaminomethyl) phenol, and a mixture thereof.

12. The bone cement composition kit of claim 8, further comprising a polymerization inhibitor, wherein the polymerization inhibitor is selected from the group consisting of hydroquinone (HQ), methyl hydroquinone (MEHQ), ascorbic acid, and a mixture thereof.

13. The bone cement composition kit of claim 8, wherein the acrylic polymer is selected from the group consisting of (A) poly(alkyl acrylates) formed from the polymerization of alkyl acrylate-based monomers; (B) copolymers formed from the copolymerization of methyl acrylate or methyl methacrylate with at least one monomer selected from styrene, ethyl methacrylate, and methyl acrylate; and (C) polymers formed from the polymerization of dimethyl acrylate-based monomers.

14. The bone cement composition kit of claim 8, wherein the acrylic monomer is selected from the group consisting of, methyl methacrylate (MMA), ethyl methacrylate (EMA), butyl methacrylate, methyl acrylate (MA), bisphenol A-diglycidyl dimethacrylate (Bis-GMA), 2,2-bis[4-(3-methyl propenoxy-2-hydroquinone propoxyl)phenyl]propane, 2,2-bis(4-methylpropenoxyethoxyphenyl)propane (Bis-MEPP), triethylene glycol dimethacrylate (TEGDMA), diethylene glycol dimethacrylate (DEGDMA), ethylene glycol dimethacrylate (EGDMA), and a combination thereof.

15. A method of treating a bone defect comprising administrating to a bone region with a defect the bone cement composition of claim 1.

16. A method of treating a bone defect comprising administrating to a bone region with a defect the bone cement composition kit of claim 8.

\* \* \* \* \*